United States Patent
Png et al.

(10) Patent No.: US 8,213,754 B2
(45) Date of Patent: Jul. 3, 2012

(54) OPTICAL SPLITTER, COMBINER AND DEVICE

(75) Inventors: Jason Png, Singapore (SG); Soon Thor Lim, Singapore (SG)

(73) Assignee: Agency for Science Technology and Research, Connexis (SG)

( * ) Notice: Subject to any disclaimer, the term of this patent is extended or adjusted under 35 U.S.C. 154(b) by 288 days.

(21) Appl. No.: 12/305,847

(22) PCT Filed: Jun. 21, 2007

(86) PCT No.: PCT/SG2007/000174
§ 371 (c)(1),
(2), (4) Date: Apr. 19, 2010

(87) PCT Pub. No.: WO2007/149055
PCT Pub. Date: Dec. 27, 2007

(65) Prior Publication Data
US 2010/0296775 A1    Nov. 25, 2010

Related U.S. Application Data

(60) Provisional application No. 60/815,317, filed on Jun. 21, 2006.

(51) Int. Cl.
*G02B 6/26* (2006.01)
(52) U.S. Cl. ......... 385/31; 385/1; 385/2; 385/3; 385/14; 385/15; 385/32; 385/39; 385/48; 385/50; 385/122; 385/129; 385/130; 385/131; 385/132
(58) Field of Classification Search .................. 385/1–3, 385/14–15, 31–32, 39, 48, 50, 122, 129–132
See application file for complete search history.

(56) References Cited

U.S. PATENT DOCUMENTS
4,278,321 A    7/1981  Mack et al.
(Continued)

FOREIGN PATENT DOCUMENTS
EP    0 263 560 A2    4/1988
(Continued)

OTHER PUBLICATIONS

Tapping Light From Waveguides by high Order Mode Exictation and Demultiplexing, Berlatzky et al, May 2006, IEEE Journal of Quantum Electronics, vol. 42, No. 5, pp. 477-482.*

(Continued)

*Primary Examiner* — Brian M. Healy
*Assistant Examiner* — Guy Anderson
(74) *Attorney, Agent, or Firm* — Buchanan Ingersoll & Rooney PC

(57) ABSTRACT

An optical splitter, a combiner and a device. The optical splitter comprises a first longitudinal waveguide for receiving an incoming light wave; at least first and second pairs of output waveguides, the output waveguides of each pair being disposed on opposite sides of the first waveguide; wherein each of the output waveguides of each pair comprises a longitudinal portion disposed parallel to the first waveguide and such that optical power is coupled from the first waveguide into the respective longitudinal portions and the longitudinal portions of output waveguides of the first and second pairs are displaced along a length of the first waveguide; wherein each of the output waveguides of each pair further comprises a substantially S-shaped portion continuing from the respective longitudinal portions and such that optical power coupling between the respective S-shaped portions of output waveguides of the first and second pairs is substantially inhibited.

11 Claims, 12 Drawing Sheets

U.S. PATENT DOCUMENTS

| | | | |
|---|---|---|---|
| 4,515,428 | A | 5/1985 | Findakly et al. |
| 4,838,636 | A | 6/1989 | Mannschke |
| 5,134,672 | A | 7/1992 | Imoto et al. |
| 5,661,825 | A * | 8/1997 | Van Dam et al. ............... 385/11 |
| 5,838,844 | A * | 11/1998 | Van Dam et al. ............... 385/14 |
| 6,201,913 | B1 | 3/2001 | Yi et al. |
| 6,731,828 | B2 * | 5/2004 | Kitou et al. ...................... 385/14 |
| 7,043,108 | B1 * | 5/2006 | Olsen ............................... 385/14 |

FOREIGN PATENT DOCUMENTS

| | | | |
|---|---|---|---|
| FR | 2741161 A1 | | 5/1997 |
| GB | 2125184 A | | 2/1984 |
| WO | WO 2006/013805 | * | 2/2006 |

OTHER PUBLICATIONS

International Search Report issued Nov. 7, 2007 in corresponding PCT/SG2007/000174.

Mouvet, C., et al., "Determination of simazine in water samples by waveguide surface plasmon resonance," *Analytica Chimica Acta*, 1997, vol. 338, pp. 109-117, Elsevier Science B.V., NL.

Clerc, D., et al., "Integrated optical output grating coupler as refractometer and (bio-)chemical sensor," *Sensors and Actuators B*, 1993, vol. 11, pp. 461-465, Elsevier Sequoia, CH.

Heideman, R.G., et al., "Performance of a highly sensitive optical waveguide Mach-Zehnder interferometer immunosensor," *Sensors and Actuators B*, 1993, vol. 10, pp. 209-217, Elsevier Sequoia, CH.

Luff, B.J., et al., "Integrated Optical Mach-Zehnder Biosensor," *Journal of Lightwave Technology*, Apr. 1998, pp. 583-592, vol. 16, No. 4, IEEE, NY, US.

Foresi, J. S., et al., "Photonic-bandgap microcavities in optical waveguides," *Nature*, Nov. 13, 1997, vol. 390, pp. 143-145, Macmillan Publishers Ltd., UK.

Ripin, Daniel J., "One-Dimensional Photonic Bandgap Microcavities for Strong Optical Confinement in GaAs and GaAs/$Al_xO_y$ Semiconductor Waveguides," *Journal of Lightwave Technology*, Nov. 1999, vol. 17, No. 11, pp. 2152-2160, IEEE, NY, US.

Png, Ching Eng, et al., "Tunable and Sensitive Biophotonic Waveguides Based on Photonic-Bandgap Microcavities," *IEEE Transactions on Nanotechnology*, Sep. 2006, vol. 5, No. 5, pp. 478-484, IEEE, NY, US.

Schmidt, Bradley, et al., "Nanocavity in a silicon waveguide for ultrasensitive nanoparticle detection," *Applied Physics Letters*, Nov. 22, 2004, vol. 85, No. 21, pp. 4854-4856, American Institute of Physics, USA.

Böttger, G., et al., "Improved transmission characteristics of moderate refractive index contrast photonic crystal slabs," *Applied Physics Letters*, Sep. 30, 2002, vol. 81, No. 14, pp. 2517-2519, American Institute of Physics, USA.

Sakai, Atsushi, et al., "Low Loss Ultra-Small Branches in a Silicon Photonic Wire Waveguide," *IEICE Trans. Electron.*, Apr. 2002, vol. E85-C, No. 4, pp. 1033-1038, Oxford University Press.

Lee, Kevin K., et al., "Effect of size and roughness on light transmission in a Si/$Si_2$ waveguide: Experiments and model," *Applied Physics Letters*, Sep. 11, 2000, vol. 77, No. 11, pp. 1617-1619, American Institute of Physics, USA.

Reed, Graham T., et al., "Issues Associated With Polarization Independence in Silicon Photonics," *IEEE Journal of Selected Topics in Quantum Electronics*, Nov./Dec. 2006, vol. 12, No. 6, pp. 1335-1344, IEEE, NY, US.

Tang, C. K., "Low-Loss, Single-Mode, Optical Phase Modulator in SIMOX Material," *Journal of Lightwave Technology*, Aug. 1994, pp. 1394-1400, vol. 12, No. 8, IEEE, NY, US.

Liao, Ling, et al., "High speed silicon Mach-Zehnder modulator," *Optics Express*, Apr. 18, 2005, vol. 13, No. 8, pp. 3129-3135, Optical Society of America, US.

Png, Ching Eng, et al., "Optical Phase Modulators for MHz and GHz Modulation in Silicon-On-Insulator (SOI)," *Journal of Lightwave Technology*, Jun. 2004, vol. 22, No. 6, pp. 1573-1582, IEEE, NY, US.

Xu, Qianfan, et al., "Micrometre-scale silicon electro-optic modulator," *Nature*, May 19, 2005, vol. 435, pp. 325-327, Nature Publishing Group, London, England.

Trinh, P. D., et al., "5×9 Integrated Optical Star Coupler in Silicon-On-Insulator Technology," *IEEE Photonics Technology Letters*, Jun. 1996, vol. 8, No. 6, pp. 794-796, IEEE, NY, US.

Barrios, C. Angulo, et al., "Electrooptic Modulation of Silicon-On-Insulator Submicrometer-Size Waveguide Devices," *Journal of Lightwave Technology*, Oct. 2003, vol. 21, No. 10, pp. 2332-2339, IEEE.

* cited by examiner

| $a_0$ / $d_0$ | 275 nm | 285 nm | 295 nm | 305 nm | 315 nm |
|---|---|---|---|---|---|
| 60 nm | 302 (95%) | 274 (96%) | 250 (98%) | 228 (98%) | 204 (98%) |
| 70 nm | 333 (91%) | 315 (94%) | 292 (90%) | 264 (98%) | 234 (98%) |
| 80 nm | 350 (80%) | 345 (85%) | 325 (90%) | 301 (94%) | 268 (97%) |
| 90 nm | 354 (61%) | 354 (66%) | 345 (72%) | 325 (80%) | 300 (87%) |

OPTICAL SPLITTER, COMBINER AND DEVICE

FIELD OF INVENTION

The present invention relates broadly to an optical splitter, to an optical combiner, and to an optical device.

BACKGROUND

In recent years, integrated optical devices have received tremendous attention as they provide low cost, high density and high data rate devices for a wide range of applications. Integrated optical devices have also been increasingly used for sensing applications because of their inherent characteristics such as high sensitivity, miniaturisation, mechanical stability and immunity to electromagnetic interference.

Optical device fabrication processes, which adopt planar CMOS technology from the mature microelectronics industry, offer ease of manufacturing and the possibility of simultaneous detection of several analytes on a single chip. Various methods have been implemented for the design of integrated optical biosensors, such as waveguide surface plasmon resonance, waveguide grating coupler, Mach-Zehnder and nanocavity.

For biosensing applications, a number of sensor configurations have been proposed, including Mach-Zehnder interferometer (MZI) and microcavity sensors.

However, most existing proposals are limited to single sensing channels. A multiple sensor device with multiple sensing channels based on such proposals typically requires one light source for each sensing channel.

In realising multiple sensing channel devices using only a single source, existing optical combiner/splitter structures have a number of disadvantages. For example, in one configuration, arrays of interconnected 3-dB couplers may be used to realise n×N couplers. Such a configuration suffers from disadvantages such as high optical losses and an accumulative size of the overall device.

Alternatively, interference based integrated n×N star couplers have been proposed. However, such couplers suffer from high optical losses and complexity of manufacturing.

A need therefore exists to provide an optical combiner/splitter structure that seeks to address at least one of the above disadvantages.

On the other hand, a need also exists to provide an active optical component for use in optical devices such as sensors or communication devices, the active optical component having improved performance in terms of at least one of attenuation and/or driving power.

SUMMARY

In accordance with a first aspect of the present invention there is provided a optical splitter comprising a first longitudinal waveguide for receiving an incoming light wave; at least first and second pairs of output waveguides, the output waveguides of each pair being disposed on opposite sides of the first waveguide; wherein each of the output waveguides of each pair comprises a longitudinal portion disposed parallel to the first waveguide and such that optical power is coupled from the first waveguide into the respective longitudinal portions and the longitudinal portions of output waveguides of the first and second pairs are displaced along a length of the first waveguide; wherein each of the output waveguides of each pair further comprises a substantially S-shaped portion continuing from the respective longitudinal portions and such that optical power coupling between the respective S-shaped portions of output waveguides of the first and second pairs is substantially inhibited.

The longitudinal portions of the output waveguides of each pair may be disposed at substantially a same distance on the opposite sides of the first way guide.

The longitudinal portions of the output waveguides of both pairs may be disposed at substantially the same distance on the opposite sides of the first waveguide.

A radius of the S-shaped portions of the output waveguides of each pair may be chosen such that optical transmission losses are reduced compared to an angled alignment of waveguide portions.

The optical splitter may be arranged for coupling substantially the same optical power from the light wave into the output waveguides.

Substantially all of an input power of the light wave may be coupled into the output waveguides.

In accordance with a second aspect of the present invention there is provided an optical combiner comprising a first longitudinal waveguide; at least first and second pairs of input waveguides, the input waveguides of each pair being disposed on opposite sides of the first waveguide; wherein each of the input waveguides of each pair comprises a longitudinal portion disposed parallel to the first waveguide and such that optical power is coupled from the respective longitudinal portions into the first waveguide and the longitudinal portions of input waveguides of the first and second pairs are displaced along a length of the first waveguide; wherein each of the input waveguides of each pair further comprises a substantially S-shaped portion continuing from the respective longitudinal portions for receiving respective incoming light waves and such that optical power coupling between the respective S-shaped portions of input waveguides of the first and second pairs is substantially inhibited.

The longitudinal portions of the input waveguides of each pair may be disposed at substantially a same distance on the opposite sides of the first way guide.

The longitudinal portions of the input waveguides both pairs may be disposed at substantially the same distance on the opposite sides of the first waveguide.

A radius of the S-shaped portions of the input waveguides of each pair may be chosen such that optical transmission losses are reduced compared to an angled alignment of waveguide portions.

Substantially all of respective input powers of the respective light waves may be coupled into the first waveguide.

In accordance with a third aspect of the present invention there is provided a n optical device comprising a waveguide formed on a substrate, the waveguide comprising a photonic bandgap structure including an optical cavity region; a highly doped cathode region formed along the waveguide and adjacent one side of the optical cavity region of the waveguide; a highly doped anode region formed along the waveguide and adjacent an opposite side of the optical cavity region of the waveguide; wherein the cathode region, the optical cavity region and the anode region form a p-i-n diode structure for controlling an attenuation characteristic of the photonic bandgap structure.

In accordance with a fourth aspect of the present invention there is provided a optical device comprising an optical splitter comprising a first longitudinal waveguide for receiving an incoming light wave, at least first and second pairs of output waveguides, the output waveguides of each pair being disposed on opposite sides of the first waveguide, wherein each of the output waveguides of each pair comprises a longitudinal portion disposed parallel to the first waveguide and such that optical power is coupled from the first waveguide into the respective longitudinal portions, and the longitudinal portions of output waveguides of the first and second pairs are displaced along a length of the first waveguide, wherein each of the output waveguides of each pair further comprises a substantially S-shaped portion continuing from the respective longitudinal portions and such that optical power coupling between the respective S-shaped portions of output waveguides of the first and second pairs is substantially inhibited; and a photonic bandgap structure optically connected to each output waveguide of the splitter, each photonic bandgap structure including a microcavity.

The optical device may further comprise an optical combiner comprising a first longitudinal waveguide, at least first and second pairs of input waveguides, the input waveguides of each pair being disposed on opposite sides of the first waveguide, wherein each of the input waveguides of each pair comprises a longitudinal portion disposed parallel to the first waveguide and such that optical power is coupled from the respective longitudinal portions into the first waveguide and the longitudinal portions of input waveguides of the first and second pairs are displaced along a length of the first waveguide, wherein each of the input waveguides of each pair further comprises a substantially S-shaped portion continuing from the respective longitudinal portions for receiving respective incoming light waves and such that optical power coupling between the respective S-shaped portions of input waveguides of the first and second pairs is substantially inhibited; and wherein the photonic bandgap structures are formed in respective optical connections between the output waveguides of the splitter and the input waveguides of the combiner.

In accordance with a fifth aspect of the present invention there is provided a optical device comprising an optical combiner comprising a first longitudinal waveguide, at least first and second pairs of input waveguides, the input waveguides of each pair being disposed on opposite sides of the first waveguide, wherein each of the input waveguides of each pair comprises a longitudinal portion disposed parallel to the first waveguide and such that optical power is coupled from the respective longitudinal portions into the first waveguide and the longitudinal portions of input waveguides of the first and second pairs are displaced along a length of the first waveguide, wherein each of the input waveguides of each pair further comprises a substantially S-shaped portion continuing from the respective longitudinal portions for receiving respective incoming light waves and such that optical power coupling between the respective S-shaped portions of input waveguides of the first and second pairs is substantially inhibited; and a photonic bandgap structure optically connected to each input waveguide of the combiner, each photonic bandgap structure including a microcavity.

BRIEF DESCRIPTION OF THE DRAWINGS

Embodiments of the invention will be better understood and readily apparent to one of ordinary skill in the art from the following written description, by way of example only, and in conjunction with the drawings, in which:

FIG. 6 shows a table summarising Q factor and transmission values.

DETAILED DESCRIPTION

Figure 1:
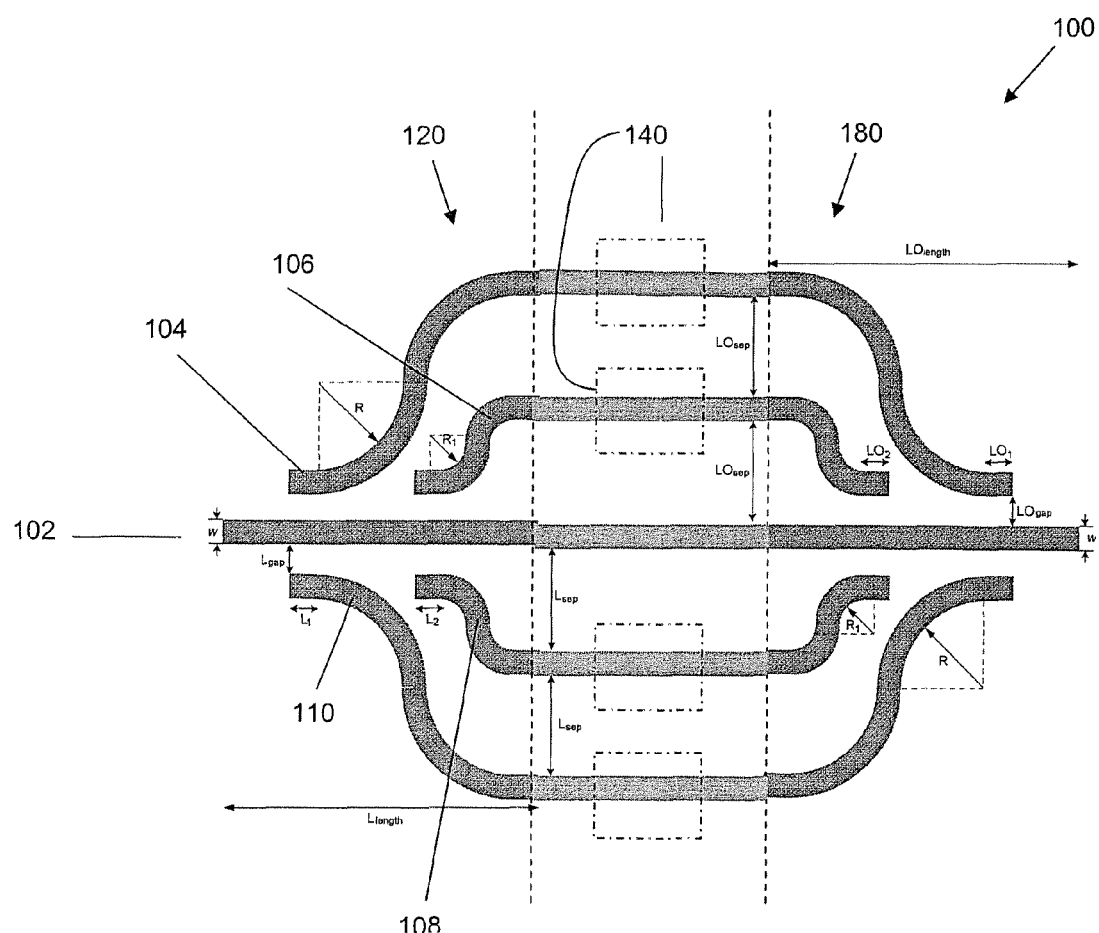
FIG. 1 shows a schematic diagram of a passive device built in accordance with one embodiment of the invention.

FIG. 1 shows a schematic diagram of a passive sensor device 100 built in accordance with one embodiment of the invention.

The passive sensor device 100 has an optical splitter 120 at the input end and an optical combiner 180 at the output end.

The passive sensor device 100 shown in FIG. 1 is of the 1×4 splitter configuration, where the passive sensor device 100 comprises a central waveguide 102 and four waveguides 104, 106, 108 and 110. A pair of the waveguides 104, 106, 108 and 110 is disposed on each side of the central waveguide 102. A passive photonic bandgap structure 140 is formed in each of the four waveguides 104, 106, 108 and 110 between the optical splitter 120 and the optical combiner 180.

One advantage of using the passive sensor device 100 is that only one light source (broad-band or tunable laser) and one detector is required, whereas conventional devices require individual light sources and detectors for each arm. As such, the passive sensor device 100 arrangement can provide cost savings.

The passive sensor device 100 has a 1×4 splitter configuration. However, it is possible to realise a 1×N splitter configuration with the appropriate design consideration, in different embodiments.

In one embodiment, the passive sensor device 100 has a semiconductor on insulator (SOI) structure, where silicon Si is used for the waveguides 102, 104, 106, 108 and 110. The waveguides 102, 104, 106, 108 and 110 are formed on an insulating $SiO_2$ layer which is formed on a Si substrate.

The form of the waveguides 102, 104, 106, 108 and 110 depends on the manufacturing material and technology and can consist of any one or more of the following shapes: ridge, channel and/or strip.

Figure 2:
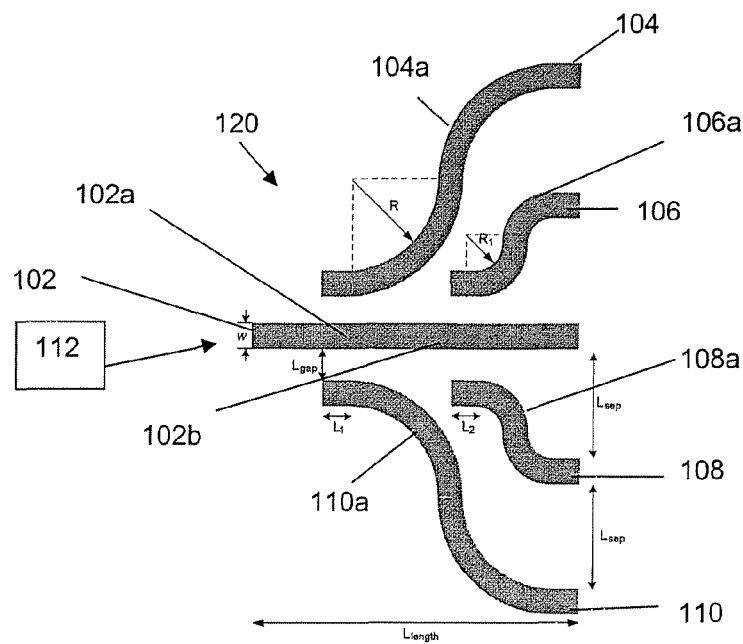
FIG. 2 shows a schematic diagram of an optical splitter.

FIG. 2 shows a schematic diagram of the optical splitter 120 of FIG. 1.

In the context of FIG. 2, the four waveguides 104, 106, 108 and 110 are more commonly referred to as splitter waveguides. The four splitter waveguides 104, 106, 108 and 110 have an S-bend arrangement in their respective regions 104a, 106a, 108a and 110a approaching the central waveguide 102. The radii of the S-bends, for instance R and $R_1$ of the splitter waveguides 104 and 106 respectively, are designed for minimum optical power loss, which is dependent on the splitter waveguides width w and the refractive index contrast ΔN of the splitter waveguides material.

The S-bend arrangement provides several advantages over a waveguide that has a straight alignment. For instance, the S-bend arrangement achieves an optical splitter with a more narrow width, thus producing an overall more compact device. Also, light travelling through the waveguide with an angled arrangement of straight waveguide portions has greater transmission loss compared to the S-bend arrangement in the example embodiment.

Substantially straight waveguides (for instance portions $L_2$ and $L_1$ of the splitter waveguides 108 and 110 respectively) are incorporated at the beginning of each of the S-bend arrangements 104a, 106a, 108a and 110a to couple optical power from the central waveguide 102 into the splitter waveguides 104, 106, 108 and 110. Optical coupling strength gradually decreases from the coupling regions 102a and 102b towards the output ends of the splitter waveguides 104, 106, 108 and 110 of the optical splitter 120.

The input ends of the four splitter waveguides 104, 106, 108 and 110 are separated a distance Lgap, from the central waveguide 102. On the other hand, a distance Lsep separates the output ends of each adjacent waveguide in the optical splitter 120. The end separation distance Lsep is selected to fulfill the criteria of zero power transfer between adjacent waveguides.

In operation, optical powers 112 with broad wavelengths are injected into the central waveguide 102. The coupling regions 102a and 102b is such that optical energy will be split substantially equally between each of the four splitter waveguides 104, 106, 108 and 110. The amplitude and phase of the optical field in each of the four splitter waveguides 104, 106, 108 and 110 is influenced by several waveguide parameters at the coupling regions 102a and 102b. These waveguide parameters include the waveguide width w, gap Lgap, height (not shown), refractive index difference (not shown) and the interactive length $L_i$ of the four splitter waveguides 104, 106, 108 and 110, where i is an integer.

The process of manufacturing the optical splitter 120 in one example embodiment utilises recticle (masks) writing for the splitter pattern using an electron-beam pattern generator. The written pattern is then transferred through photolithography. A SOI wafer is first coated with photoresist, followed by the transfer of the pattern through photolithograpy. Anisotropic etching is performed to remove silicon in the exposed areas, hence creating the Si waveguides of the optical splitter 120 on the wafer. This is followed by stripping the remaining resist from the wafer.

Figure 3:
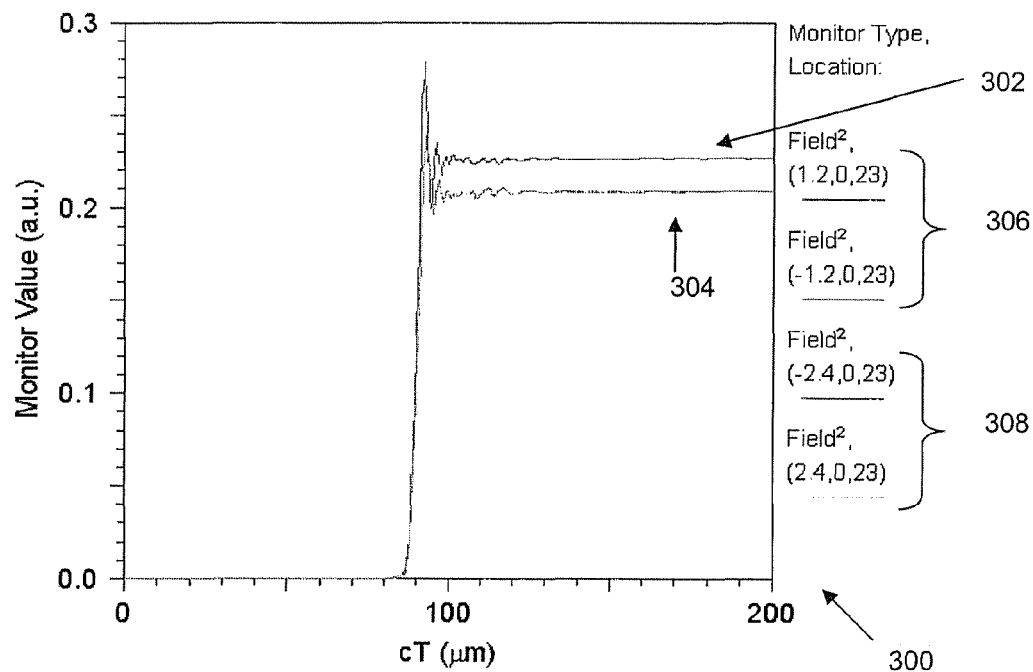
FIG. 3 shows a plot of normalised power against cT.

FIG. 3 shows a plot 300 of normalised power against cT, where cT is the unit of time used in the computational calculation, where c is the speed of light in vacuum The plot 300 illustrates simulation results of the normalised power in each of the four splitter waveguides 104, 106, 108 and 110 (FIG. 2) of the optical splitter 120 (FIG. 2) having a silicon-on-insulator (SOI) structure with the following parameters:

w=500 nm, si-overlayer=220 nm, Lgap=0.1 μm, $L_1$=3.1 μm, $L_2$=8 μm, Lsep=0.7 μm The Finite Differential Time Domain (FDTD) Method was used to observe the power transfer effect occurring in the optical splitter 120 (FIG. 2). This method is useful for analysis of small cross sectional wave-guiding structures. First, modal analysis is used to solve the fundamental mode in a photonic wire. This fundamental mode is then used as a launch file to solve for the optical splitter structure in question. This way, the loss of the structure in question is computed due to device configuration and not the loss inherent by the waveguide structure caused by modal mismatch.

Numerals 302 and 304 indicate overlapping curves for the simulation results obtained from the splitter waveguides 104, 110 and 106, 108 (FIG. 2) respectively. In other words, the curves for the pair 306 of waveguides 104, 110 (FIG. 2) overlap, and the curves for the pair 308 of waveguides 106, 108 (FIG. 2) overlap. FIG. 3 illustrates that each of the four splitter waveguides 104, 106, 108 and 110 (FIG. 2) has an output normalised power of approximately 0.22. The result obtained agrees well with calculation based on parallel coupling using coupled mode theory.

Coupled mode theory specifies that when two waveguides are brought close together, optical modes of each waveguides either couple or interfere with each other. The coupled mode equations are given by:

$$\frac{dA}{dz} = -jk_{12}B\exp[-j(\beta_2 - \beta_1)z] \quad (1)$$

$$\frac{dB}{dz} = -jk_{21}A\exp[-j(\beta_2 - \beta_1)z] \quad (2)$$

where β is the propagation constant. The solutions, with the assumption of $\beta_1$ and $\beta_2$ are greater than zero, can be expressed as:

$$A(z) = [a_1 e^{-jqz} + a_2 e^{-jqz}] \exp(-j\delta z) \quad (3)$$

$$B(z) = [b_1 e^{-jqz} + b_2 e^{-jqz}] \exp(j\delta z) \quad (4)$$

where q is an unknown parameter to be determined. Constants $a_1$, $a_2$, $b_1$, and $b_2$ should satisfy the initial conditions:

$$a_1 + a_2 = A(0) \quad (5)$$

$$b_1 + b_2 = B(0) \quad (6)$$

Substituting Eqs. (3) and (4) into Eqs. (1) and (2) and applying the initial conditions from Eqs. (5) and (6) yield the following equations:

$$A(z) = \left\{\left[\cos(qz) + j\frac{\delta}{q}\sin(qz)\right]A(0) - j\frac{\kappa}{q}\sin(qz)B(0)\right\}\exp(-j\delta z) \quad (7)$$

$$B(z) = \left\{-j\frac{\kappa}{q}\sin(qz)A(0) + \left[\cos(qz) - j\frac{\delta}{q}\sin(qz)\right]B(0)\right\}\exp(j\delta z) \quad (8)$$

where q is given by $q = \sqrt{\kappa^2 + \delta^2}$ and k is the coupling coefficient.

If light is coupled into the adjacent waveguide only at z=0, this yields the conditions of $A(0) = A_0$ and $B(0) = 0$. The optical power flow along the z-direction is given by:

$$P_a(z) = \frac{|A(z)|^2}{|A_o|^2} = 1 - F\sin^2(qz) \quad (9)$$

$$P_B(z) = \frac{|B(z)|^2}{|A_o|^2} = F\sin^2(qz) \quad (10)$$

where F is the maximum power-coupling efficiency, defined by $$F = \left(\frac{\kappa}{q}\right)^2 = \frac{1}{1+(\delta/\kappa)^2} \quad (11)$$

Figure 4:
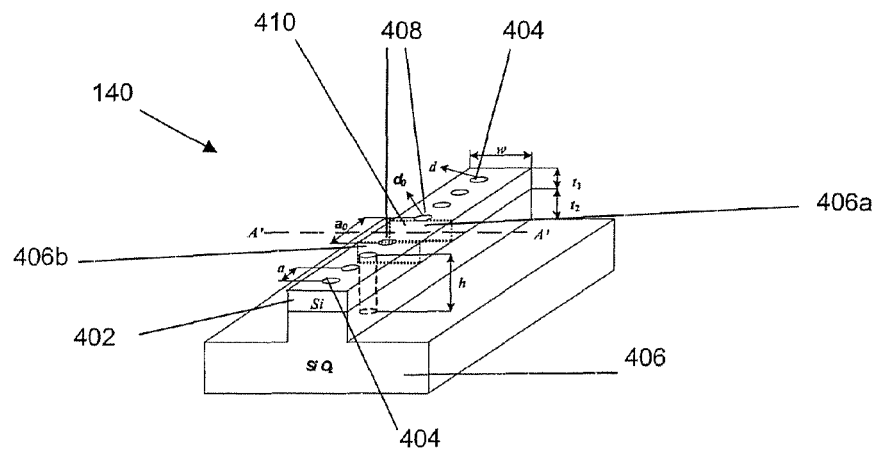
FIG. 4 shows a cross sectional view of a photonic bandgap structure.

FIG. 4 shows a cross sectional view of one of the four passive photonic bandgap structures 140 of FIG. 1.

The passive photonic bandgap structure 140 has a SOI structure. The passive photonic bandgap structure 140 comprises a silicon layer 402 formed above an insulating $SiO_2$ layer 406.

The silicon layer 402 has arrays of 1-D periodic air holes 404 formed in the silicon layer 402, with a microcavity 410 breaking the periodicity of the airholes. The airholes that are immediately adjacent to the microcavity 410 are given the reference numeral 408.

The microcavity 410 acts as a defect within the silicon layer 402 that causes a state that is analogous to the formation of a level within a semiconductor bandgap. In this manner, the silicon layer 402 acts as a photonic crystal waveguide with a defect in the mid section. The light confinement capability of the microcavity 410 induces a strong electric field in the microcavity 410 which is stronger than the electric field inside the remainder of the silicon layer 402. By removing the cladding (not shown) above the microcavity 410, the induced electric field of the microcavity 410 enhances the effective cross section of analytes that are present above the surface of the photonic bandgap device 100 (FIG. 1) when the photonic bandgap device 100 (FIG. 1) is used as a biosensor. Thus, when an analyte is present in the vicinity of the microcavity 410, optical light being transmitted through the microcavity 140 becomes attenuated. A drop in the output power of the photonic bandgap device 100 (FIG. 1) thus indicates that analytes are detected. As one microcavity 410 exists along each of the four splitter waveguides 104, 106, 108 and 110 (FIG. 1), the passive sensor device 100 (FIG. 1) can be applied, e.g. as a multiple sensing arm biosensor using only one light source and detector pair. By choosing each microcavity 410 to exhibit a different transmission wavelength, one broadband light source can be placed at the input side and a detector in the form of a spectrum analyser can be placed at the output side to monitor the response of the respective wavelengths along each respective sensing arm.

A Bragg mirror-like response is present on both sides 406a and 406b of the microcavity 410. The air holes 408 that are immediately adjacent to the microcavity 410 have a different diameter than the diameter of the remaining air holes 404. The air holes 408 are commonly referred to as the innermost air holes. Unlike conventional photonic crystal waveguides, where the air holes are etched only into the silicon layer, the air holes 404 and 408 are etched a depth within the $SiO_2$ layer 402. This "etch-down" design improves the transmission property of the photonic crystal waveguide 402. This "etch-down" design also prevents the wave travelling inside the silicon layer 402 from leaking into the $SiO_2$ layer 406. In preventing wave leakage, the "etch-down" design was found as effective as the known "air-bridge" design, where in the "air-bridge" design an air gap is formed beneath the microcavity structure. However, the "etch-down" design is simpler to fabricate.

The formation of the airholes 404 and 408 are to limit the wave vector factor inside the photonic crystal waveguide 402. The airholes 404 and 408 also produce an evanescent field that facilitates coupling of the waveguide modes in the photonic crystal waveguide to the microcavity 410.

The symbols used to demarcate the various dimensions of the photonic crystal waveguide 402 are summarised as follows: $a_0$ is the length of the microcavity 410; a is the period of the air holes; $d_0$ is the diameter of the two air holes 408 immediately adjacent to the microcavity 410; d is the diameter of the remaining air holes 404; w is the width of the photonic crystal waveguide 402; $t_1$ is the thickness of the photonic crystal waveguide 402; $t_2$ is the etching depth of the $SiO_2$ layer 406; and h is the etching depth of the air holes 404 and 408.

From running simulations using a 3-D FDTD package from CST Microwave Studio, it was found that an optimum etching depth h for the air holes 404 and 408 was 400 nm, which produced a Q factor of around 320, for $a_0$=295 nm, a=180 nm, $d_0$=80 nm, d=68 nm, w=475 nm, $t_1$=400 nm and $t_2$=400 nm. The Q factor is a measure of the strength of the relative linewidth. The 0 factor is the ratio of the resonance frequency, v and the (full width at half maximum) bandwidth dv of the resonance, i.e.

$$Q\text{ factor}=v/dv \quad (12)$$

Varying the etching depth h from 400 nm to 550 nm did not provide any obvious improvement, where the power transmission at resonance remained almost unchanged.

The transmission property for the photonic bandgap structure 140 was simulated using the 3-D FDTD package from CST Microwave Studio. An etching depth h of 400 nm was used. The simulation was conducted using diameter $d_0$ values 60, 70, 80 and 90 nm for the air holes 408, and respective length $a_0$ values 275, 285, 295, 305 and 315 nm for the microcavity 410. The results of the simulation are shown in FIG. 5, for a=180 nm, $d_0$=80 nm, d=68 nm, w=475 nm, $t_1$=400 nm and $t_2$=400 nm.

Figure 5:
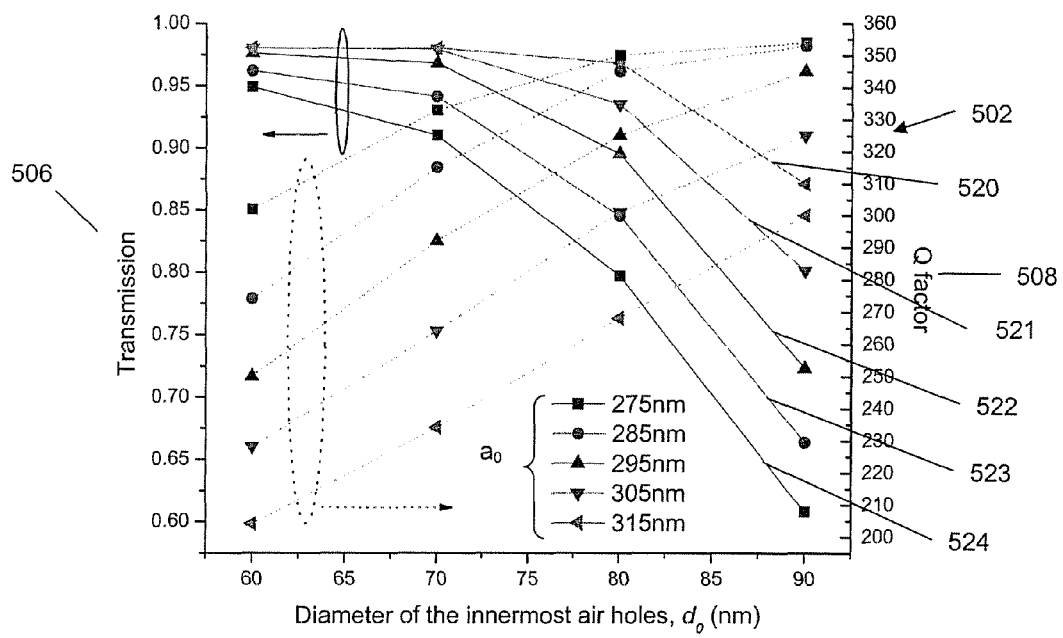
FIG. 5 shows a plot of transmission and Q factor.

FIG. 5 shows a plot 502 of the transmission 506 and Q factor 508 against the diameter $d_0$ of the innermost air holes 408 of the photonic bandgap structure 140 of FIG. 4. FIG. 5 also shows how varying the length $a_0$ of the photonic bandgap structure 140 (FIG. 4) affects both the transmission 506 and the Q factor 508 characteristics of the photonic bandgap structure 140 (FIG. 4). Graphs 520, 521, 522, 523 and 524 show the range of transmission 506 and factor 508 values for varying the diameter $d_0$ for cavity lengths $a_0$ of 315, 305, 295, 285 and 275 nm respectively.

From FIG. 5, it can be observed that the factor 508 decreases when the length $a_0$ increases. This is because the optical mode is not as well confined in the microcavity 410 (FIG. 4) when the length $a_0$ increases. Transmission 506 characteristics improve when the length $a_0$ is increased. The Q factor 508 reduces when the diameters $d_0$ are reduced. When the diameter $d_0$ is reduced, the optical throughput also increases. Thus, the transmission 506 and Q factor 508 characteristics share an inverse relationship.

The above simulation results are summarised in Table 600 shown in FIG. 6. Both the transmission 506 values and the Q factor 508 values of FIG. 5A are tabulated in table 520 against their respective lengths $a_0$ and diameters $d_0$. The transmission 506 values are placed in brackets in table 600. It will be appreciated, from table 600, that a range of device parameters can be chosen to obtain a high Q factor 508 and high transmission 506 properties by tuning the microcavity length $a_0$ and the air holes diameters $d_0$. For example, when length $a_0$=295 nm and diameter $d_0$=80 nm, we obtain a Q factor 508 of around 325 and a corresponding transmission 506 of around 90%. Another example would be when length $a_0$=275 nm and diameter $d_0$=70 nm, we obtain a Q factor 508 of around 333 and a corresponding transmission 506 of around 91%.

For a sub-micrometer height of 400 nm, high scattering loss is dominated by the microcavity 410 (FIG. 4) waveguide sidewall roughness. The documents "Low loss ultra-small branches in a silicon photonic wire waveguide," *IEICE Trans. Electron.*, vol. E85-C, pp. 1033-1038, 2002 by Sakai et al. and "Effect of size and roughness on light transmission in a $Si/SiO_2$," by Lee et al. discuss the relationship between waveguide losses and waveguide dimensions to enable the design and fabrication of a waveguide in SOI with minimal loss, where 0.1 dB/cm transmission loss was demonstrated for a device with a Si layer height of 200 nm in the latter document. As such, it is feasible to use a 400 nm thick Si layer ($t_i$) for the microcavity 410. The results discussed above pertain to TE polarization optical signals in the example embodiments. However, polarisation independent SOI waveguides can also be formed, e.g. based on the technique described in S. P. Chan, C. E. Png, S. T. Lim, G. T. Reed, V. M. N. Passaro, "Single Mode and Polarisation Independent Silicon-on-Insulator Waveguides with Small Cross Section", IEEE J. of Lightwave Tech. 23, 2103-2111 (2005). Polarization independent waveguides may be incorporated in different embodiments for fabrication of polarization independent devices.

Figure 7:
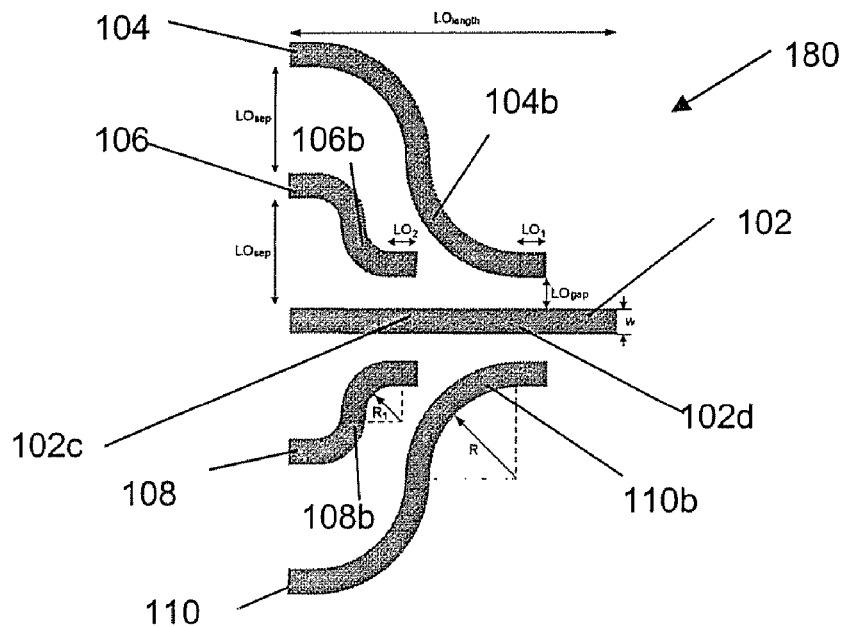
FIG. 7 shows a schematic diagram of an optical combiner.

FIG. 7 shows a schematic diagram of the optical combiner 180 of FIG. 1. It will be appreciated that the optical combiner 180 has an inverse configuration to the optical splitter 120 of FIG. 2. Thus, the optical combiner 180 has corresponding parameters to that of the optical splitter 120 (FIG. 2).

In the context of FIG. 7, the four waveguides 104, 106, 108 and 110 are more commonly referred to as combiner waveguides. The four combiner waveguides 104, 106, 108 and 110 have an S-bend arrangement in their respective regions 104b, 106b, 108b and 110b approaching the output portion of the central waveguide 102. The radii of the S-bends, for instance R and $R_1$ of the combiner waveguides 110 and 108 respectively, are designed for minimum optical power loss, which is dependent on the combiner waveguides width w and the refractive index contrast ΔN of the combiner waveguide material.

Substantially straight waveguides (for instance portions $LO_2$ and $LO_1$ of the splitter waveguides 106 and 104 respectively) are incorporated at the end of each of the S-bend arrangements 104b, 106b, 108b and 110b to couple optical power from each of the splitter waveguides 104, 106, 108 and 110 into the central waveguide 102.

The output ends of the four combiner waveguides 104, 106, 108 and 110 are separated a distance LOgap, from the central waveguide 102. On the other hand, a distance LOsep separates the beginning portions of each adjacent waveguide in the optical combiner 180. The separation distance LOsep is selected to fulfill the criteria of zero power transfer between adjacent waveguides.

Figure 8:
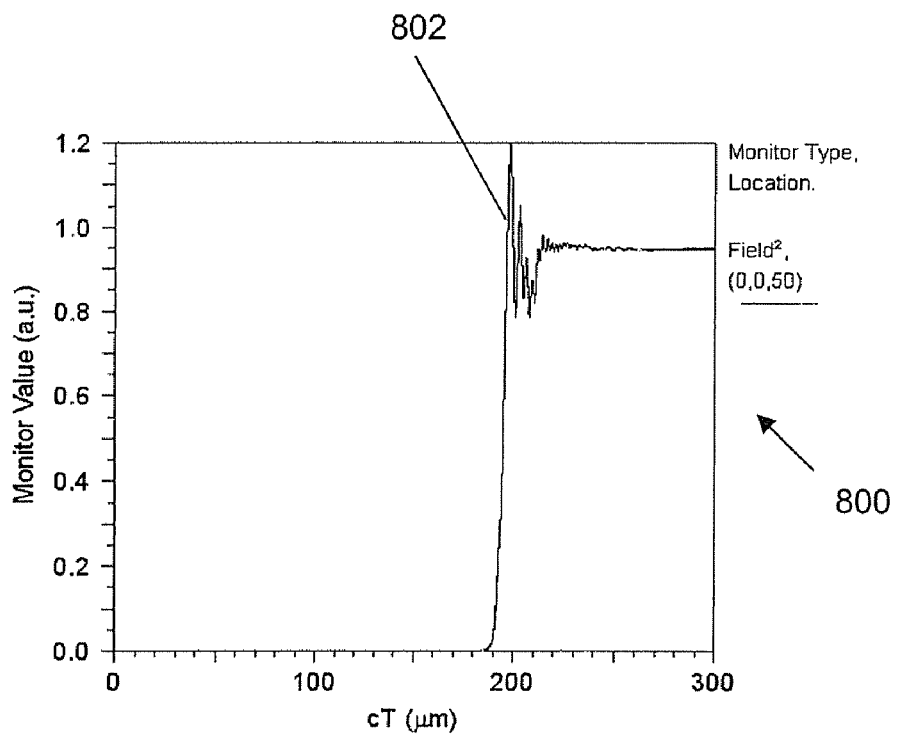
FIG. 8 shows a plot of normalised power against cT

FIG. 8 shows a plot 800 of normalised power against cT. The plot 800 illustrates results, using the FDTD simulation method, of the total normalised output power from the central waveguide 102 of the optical combiner 180 of FIG. 8. The simulated optical combiner 180 (FIG. 7) had a silicon-on-insulator (SOI) structure with the following parameters:

w=500 nm, si-overlayer=220 nm, Lgap=0.1 µm, $L_1$=3.1 µm, $L_2$=8 µm, Lsep=0.7 µm The FDTD simulation was conducted to investigate the effectiveness of the optical coupling between the four combiner waveguides 104, 106, 108 and 110 and the central waveguide 102. Curve 802 shows that the output from the optical combiner 180 has a normalised power of 0.95.

It will be appreciated that the optical splitter and the optical combiner discussed above can be used in a number of device applications, including, e.g. in optical multiplexers and optical demultiplexers.

Figure 9:
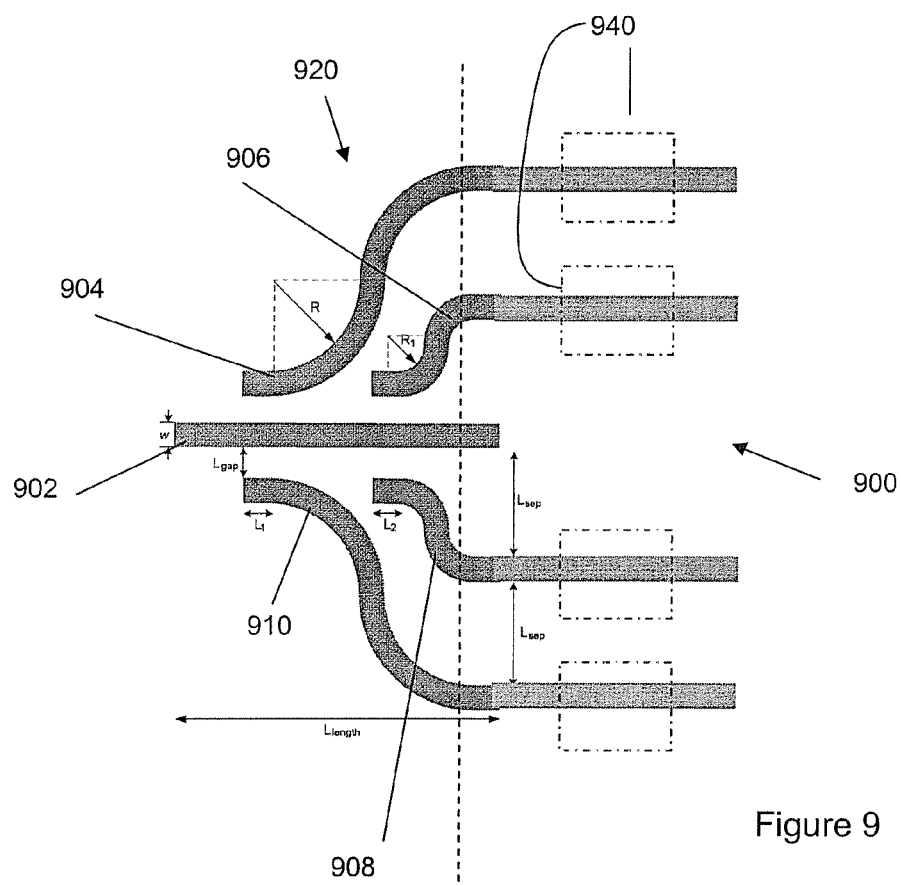
FIG. 9 shows a schematic diagram of an optical demultiplexer built in accordance with one embodiment of the invention.

FIG. 9 shows a schematic diagram of an optical demultiplexer 900 built in accordance with one embodiment of the invention.

The optical demultiplexer 900 shown in FIG. 9 is of the 4 channel configuration. However, it will be appreciated that it is possible to realise an N=4, 6, 8, 10, . . . etc channel configuration with the appropriate design consideration, in different embodiments. The optical demultiplexer 900 has an optical splitter 920 having a central waveguide 902 and four waveguides 904, 906, 908 and 910. A photonic bandgap structure 940 is formed in each of the four waveguides 904, 906, 908 and 910.

Optical energy injected into the central waveguide 902 will be equally split into each of the four waveguides 904, 906, 908 and 910. The photonic bandgap structure 940 acts as an optical filter for the respective channel wavelengths.

Figure 10:
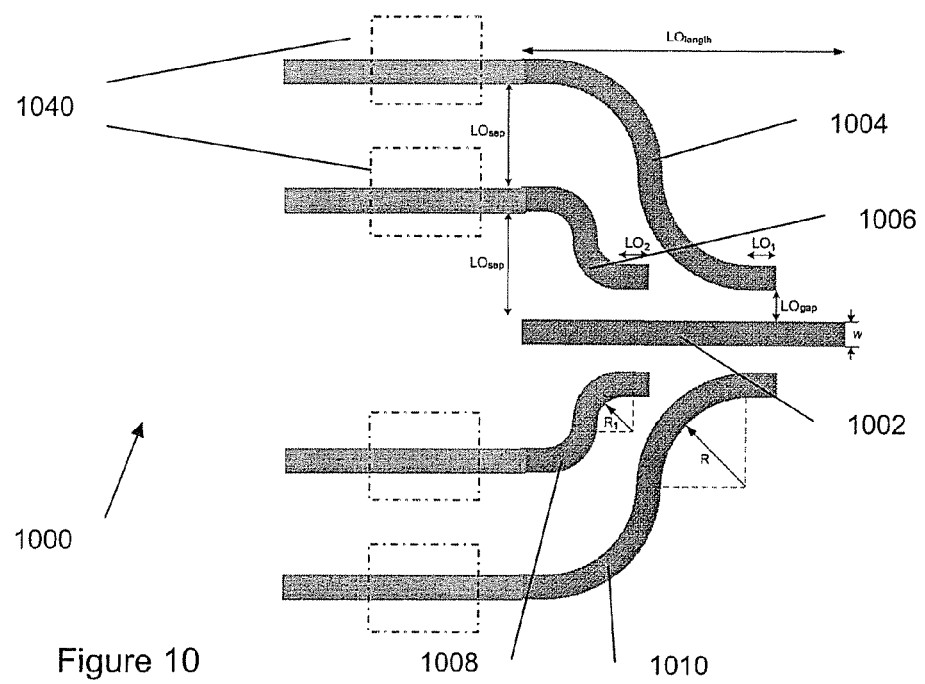
FIG. 10 shows a schematic diagram of an optical multiplexer built in accordance with one embodiment of the invention.

FIG. 10 shows a schematic diagram of an optical multiplexer 1000 built in accordance with one embodiment of the invention.

The optical multiplexer 1000 shown in FIG. 10 is of the 4 channel configuration. However, it will be appreciated that it is possible to realise an N=4, 6, 8, 10, . . . etc channel configuration with the appropriate design consideration, in different embodiments. The optical multiplexer 1000 has an optical combiner 1080 having a central waveguide 1002 and four waveguides 1004, 1006, 1008 and 1010. A photonic bandgap structure 1040 is formed in each of the four waveguides 1004, 1006, 1008 and 1010.

The photonic bandgap structure 1040 acts as an optical filter for the respective channel wavelengths. Resulting optical energy that is transmitted from each photonic bandgap structure 1040 on each of the four waveguides 1004, 1006, 1008 and 1010 will be combined into the central waveguide 1002.

Figure 11:
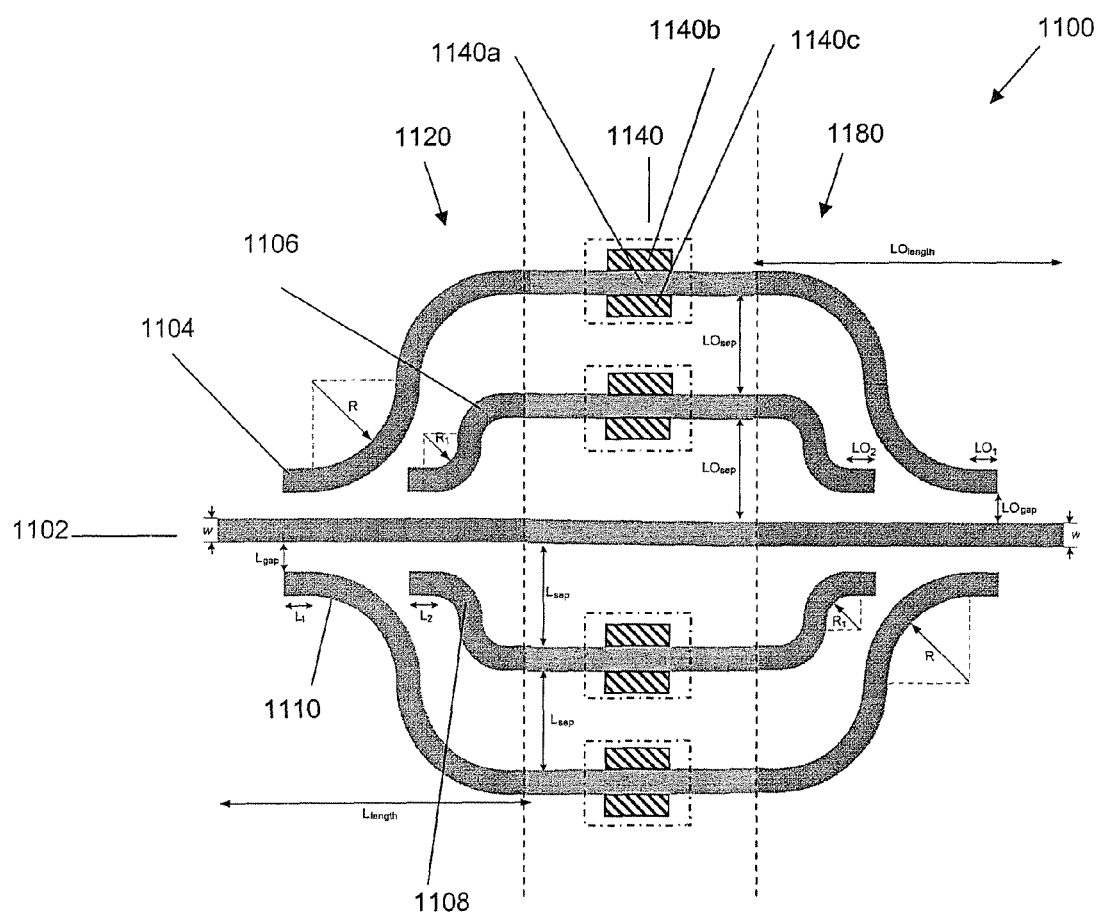
FIG. 11 shows a schematic diagram of an active device built in accordance with one embodiment of the invention.

In another application, the optical splitter and combiner can be used in an active attenuation device 1100 as shown in FIG. 11 for one embodiment of the invention.

The active attenuation device 1100 has an optical splitter 1120 at the input end and an optical combiner 1180 at the output end.

The active attenuation device 1100 shown in FIG. 11 is of the 1×4 splitter configuration, where the active attenuation device 1100 comprises a central waveguide 1102 and four waveguides 1104, 1106, 1108 and 1110. A pair of the waveguides 1104, 1106, 1108 and 1110 is disposed on each side of the central waveguide 1102. An active photonic bandgap structure 1140 is formed in each of the four waveguides 1104, 1106, 1108 and 1110 between the optical splitter 1120 and the optical combiner 1180.

The active attenuation device 1100 has a 1×4 splitter configuration. However, it is possible to realise a 1×N, N=4, 6, 8, 10, . . . etc splitter configuration with the appropriate design consideration, in different embodiments.

It will be appreciated that the optical splitter 1120 and the optical combiner 1180 have similar structures, dimensions and fabrication methodology to both the optical splitter 120 and the optical combiner 180 of FIG. 1 respectively. The active photonic bandgap structure 1140 includes a photonic bandgap structure similar to the photonic bandgap structure 140 of FIG. 1, but the microcavity 1140a of the active photonic bandgap structure 1140 has adjacent cathode and anode regions 1140b and 1140c.

Figure 12:
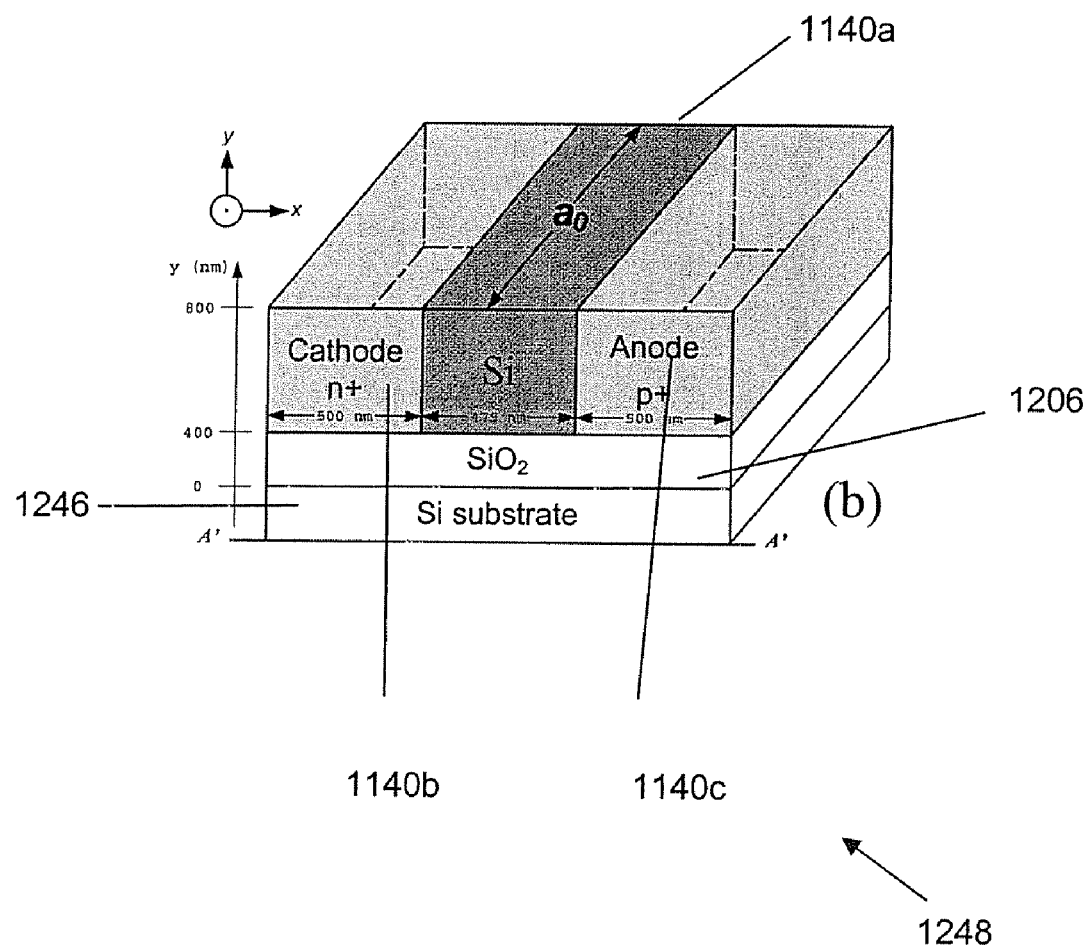
FIG. 12 shows across sectional view of a microcavity of an active device.

FIG. 12 shows a cross sectional view of a microcavity 1140a of the active attenuation device 1100 of FIG. 11.

The cathode and anode regions 1140b and 1140c, and the microcavity 1140a are formed above a $SiO_2$ layer 1206, where both the cathode region 1140b and the anode region 1140c are adjacent to and in contact with the microcavity 1140a. The SiO$_2$ layer 1206 is formed above a Si substrate 1246.

In one example embodiment, fabrication of the p+ (anode) and n+ (cathode) contacts 1140c, 1140b will now be described. Initially, the designated n+ region is covered by deposition of a 500 nm oxide layer by oxidation using plasma enhanced chemical vapour deposition (PECVD), and exposing only the designated p+ region through patterning and etching.

The p+ region is realised with the growth of 400 nm of highly doped Si in the exposed region by selective epitaxy at $1 \times 10^{20}$ atoms/cm$^3$ (Boron). In instances where the epitaxy equipment used has a limited target concentration (e.g. can only reach up to $1 \times 10^{19}$ atoms/cm$^3$), an implantation step of Boron at an appropriate dosage to increase the net dopant concentration to $1 \times 10^{20}$ atoms/cm$^3$ can be included. The p+ region is then protected with 500 nm silicon dioxide using PECVD.

The silicon dioxide at the designated n+ region is then etched off. The n+ region is realised with the growth of 400 nm of highly doped Si in the exposed region by selective epitaxy at $1 \times 10^{20}$ atoms/cm$^3$ (Arsenic and Phosphorous). In instances where the epitaxy equipment used has a limited target concentration (e.g. can only reach up to $1 \times 10^{19}$ atoms/cm$^3$), and an implantation step of Arsenic or Phosphorus at an appropriate dosage to increase the net dopant concentration to $1 \times 10^{20}$ atoms/cm$^3$ can be included. The n+ region is then protected with 500 nm silicon dioxide using PECVD.

Where dopant implantation is performed in the fabrication of the n+ region, the p+ region, or both, an appropriate annealing step may be required to restore the crystal lattice to its original state and to activate the implanted carriers.

Next, a layer of 300 nm oxide is deposited over the wafer and then planarised using chemical mechanical polishing (CMP) in preparation of metallisation using deposition contact lithography and dry etching, followed by an alloy and anneal at 350° C. for 30 mins, to segregate the anode and cathode regions.

It is noted that the fabrication order of the n+ and p+ regions can be interchanged to increase flexibility in different embodiments.

Collectively, the anode region 1140c, the microcavity 1140a and the cathode region 1140b form an active p-i-n diode 1248. The active diode 1248 provides optical switching capability via the free carrier injection effect. This involves biasing the active diode 1248 so that carriers are injected into the microcavity 1140a which causes attenuation of the optical signal being transmitted through the microcavity 1140a.

In the embodiment shown in FIG. 12, the cathode region 1140b and the anode region 1140c are highly doped regions with constant doping concentrations of $10^{20}$ cm$^{-3}$. The SiO$_2$ layer 1206 and the active diode 1248 each have a thickness of around 400 nm. The cathode region 1140b and the anode region 1140c have a width of around 500 nm each, while the microcavity 1140a has a width of around 475 nm. The microcavity 1140a has a length $a_0$.

The dc and transient characteristics of the active diode 1248 was investigated using a 2-D ATLAS device simulation package from SILVACO. The results are discussed with reference to FIGS. 13, 14 and 15.

Figure 13:
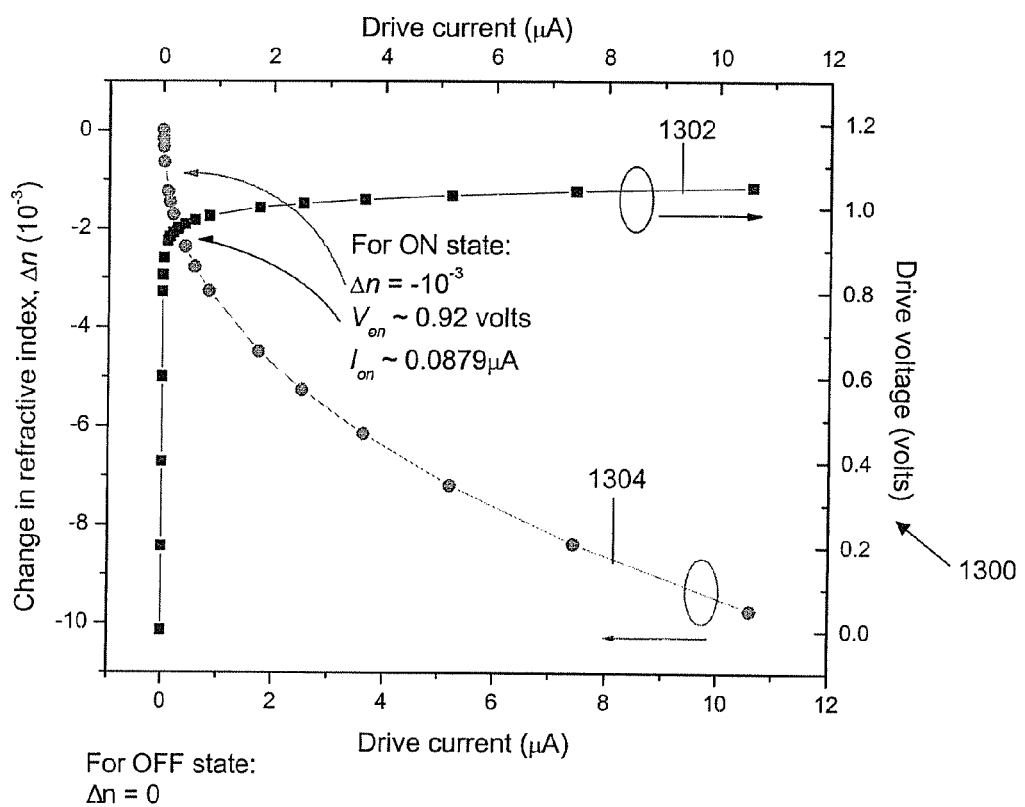
FIG. 13 shows a plot of drive voltage against drive current and a respective change in refractive index, $\Delta n$.

FIG. 13 shows a plot 1300 of drive voltage (V) against drive current (I) and a respective change in refractive index, Δn.

Curve 1302 shows the I-V relationship for the active diode 1248 of FIG. 12. From curve 1302, it is observed that in the OFF state, i.e. when there is no carrier injection into the active diode 448, there is no change in the refractive index, Δn. In the ON state, designated here as where $N_e$ (concentration of electrons)=$N_h$ (concentration of free holes)≈$3 \times 10^{17}$ cm$^{-3}$, there is a change in refractive index, Δn, of approximately $10^{-3}$. The applied current and voltage required to achieve the ON state are 0.92 volts and 0.0879 µA respectively, corresponding to an applied power of around 80.9 nW.

Curve 1304 shows the static performance of the active diode 1248 of FIG. 12, which indicates the change in refractive index, Δn, and hence phase change, varies nonlinearly with the applied current. One factor, which contributes to the nonlinearity of the change in phase versus current density relationship, is the sublinear dependence of the change in concentration of the free holes, $\Delta N_h$, with the change in refractive index, Δn. As the active diode 1248 is driven harder, more free carriers are injected into the intrinsic region (the microcavity 1140a) of the active diode 1248. This increase in the concentration of the previously intrinsic region results in an increase in the Auger recombination rate (at injected carrier concentrations much greater than $10^{17}$ cm$^{-3}$ the Auger recombination becomes the dominant recombination process). This results in a reduced carrier lifetime in the intrinsic region. The active diode 1248 has thus to be driven harder to achieve an equivalent refractive index change, Δn, than at lower drive powers. An increase in the recombination rate will result in the active diode 1248 becoming a faster switching device, i.e. a reduction in the rise and fall times of the active diode 1248.

Figure 14:
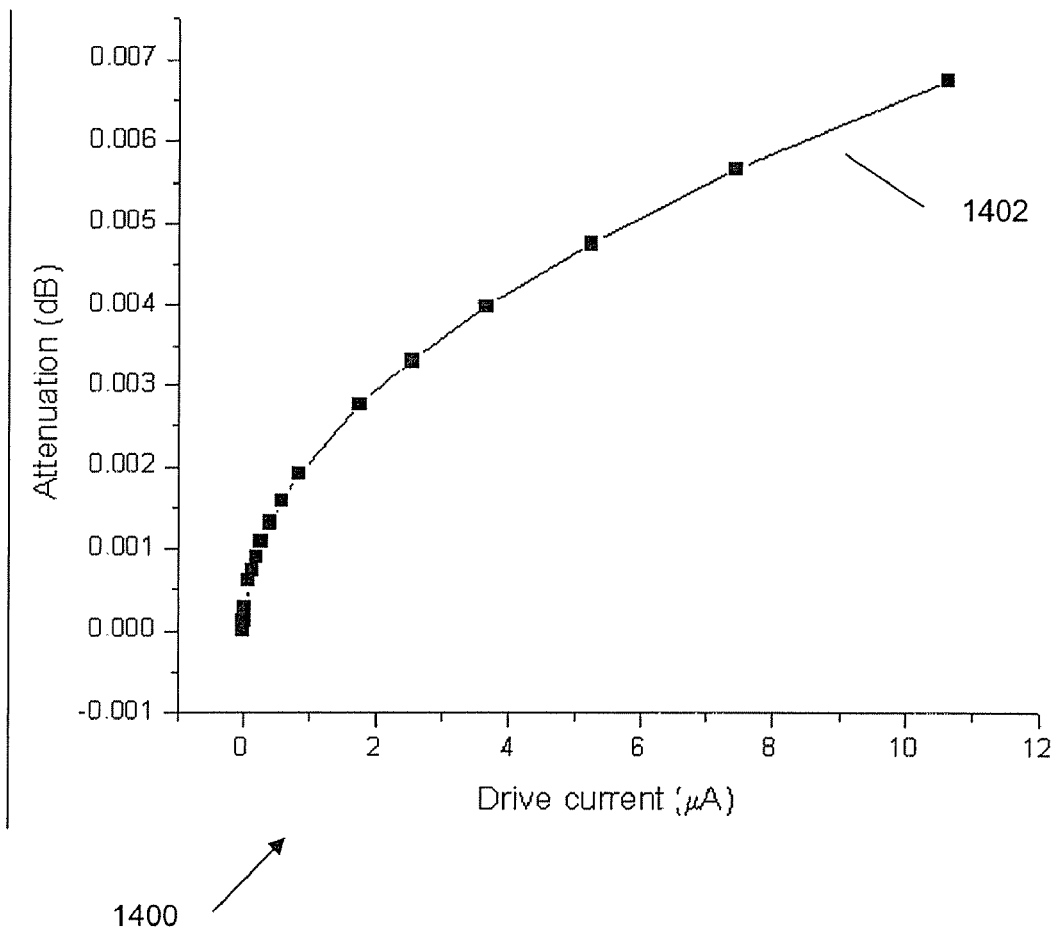
FIG. 14 shows a plot of attenuation against drive current.

FIG. 14 shows a plot of attenuation (dB) against drive current (µA). Curve 1402 shows the attenuation experienced by an optical signal propagating through the microcavity 1140a of FIG. 12 of length $a_0$ 275 nm. From FIG. 14, it is observed that attenuation increases as the active diode 1248 is driven harder.

For example, by driving the device to produce an injection level off $3.9 \times 10^8$, which corresponds to an applied voltage of around 1.05V, the attenuation is given by:

$$\Delta \alpha = \Delta \alpha_e + \Delta \alpha_h \qquad (13)$$
$$= 8.5 \times 10^{-18} \cdot \Delta N_e + 6.0 \times 10^{-18} \cdot \Delta N_h$$
$$= 8.5 \times 10^{-18} \cdot (3.9 \times 10^8) + 6.0 \times 10^{-18} \cdot (3.9 \times 10^8)$$
$$= 56.3 \text{ cm}^{-1}$$

This is equivalent to 244 dB/cm, which is in turn equivalent to 6.72e-3 dB for the microcavity 1140a (FIG. 12) length $a_0$ of 275 nm, or 1.34e-2 dB for a microcavity 1140a (FIG. 12) length $a_0$ of 550 nm. Such attenuation is about 5 orders of magnitude greater than existing attenuators, such as existing fiber based photonic bandgap attenuators or Si rib or strip waveguide based attenuators. It will also be appreciated that attenuation can be increased by lengthening the microcavity 1140a (FIG. 12).

Figure 15:
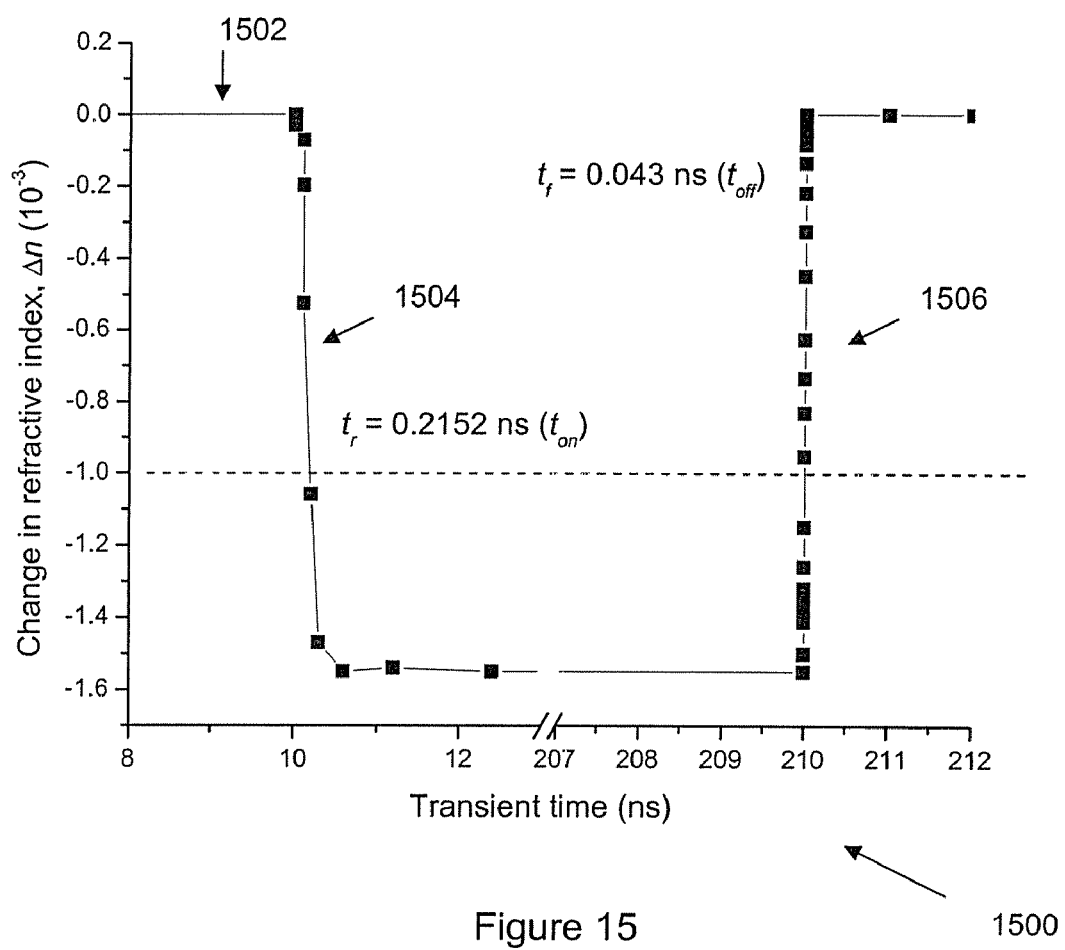
FIG. 15 shows a plot of the change in refractive index, $\Delta n$, against transient time for an active diode.

FIG. 15 shows a plot 1500 of the change in refractive index, Δn, against transient time for the active diode 1248 of FIG. 12. The plot 1500 is used to evaluate the dynamic performance of the active diode 1248 (FIG. 12) by investigating the switching speed exhibited by a transient modelling solution. Both the anode region 1140c (FIG. 12) and the cathode region 1140b (FIG. 12) were first zero biased 1502 for 10 ns, followed by a step increase 1504 to a voltage $V_\pi$ for 200 ns, and a subsequent step decrease 1506 to a voltage 0V. $V_\pi$ is the voltage corresponding to a 180° phase shift and is about 0.92V from FIG. 13. The rise time, $t_r$, is defined as the time required for the induced phase shift to change from 10% to 90% of the maximum value. Likewise, the fall time, $t_f$, is defined as the time required for the induced phase shift to change from 90% to 10% of the maximum value. For the active diode 1248 (FIG. 12), the rise and fall times were determined to be $t_r$=0.215 ns and $t_f$=0.043 ns respectively.

The dynamic optical absorption introduced by switching the device ON (step increase 1204) corresponds to $N_e = N_h \approx 3 \times 10^{17}$ cm$^{-3}$. Using equation (14), $$\Delta a = \Delta a_e + \Delta a_h = 8.5 \times 10^{-18} (\Delta N_e) + 6.0 \times 10^{-18} (\Delta N_h) \quad (14)$$

where $\Delta N_e$ (cm$^{-3}$) is the electron concentration change; $\Delta N_h$ (cm$^{-3}$) is the hole concentration change; $\Delta a_e$ (cm$^{-1}$) is the absorption coefficient variation due to $\Delta N_e$; and $\Delta a_h$ (cm$^{-1}$) is the absorption coefficient variation due to $\Delta N_h$, this injection of both electrons and holes translate to an additional absorption loss of approximately 4.35 cm$^{-1}$ (i.e. 18.9 dB/cm). This results in a dynamic optical absorption of approximately 0.0005 dB if the microcavity 1140a (FIG. 12) length $a_0$ is around 275 nm.

The optical attenuation can be improved by optimising the position of the dopant contact windows for both the anode region 1140c (FIG. 12) and the cathode region 1140b (FIG. 12). The active diode 1248 (FIG. 12) switching performance can also be improved, without changing its physical dimensions, by overdriving during the rise and fall times (steps 1204 and 1206 respectively). However, overdriving has the disadvantage of increasing the complexity of the active attenuation device 1100 (FIG. 11).

Figure 16:
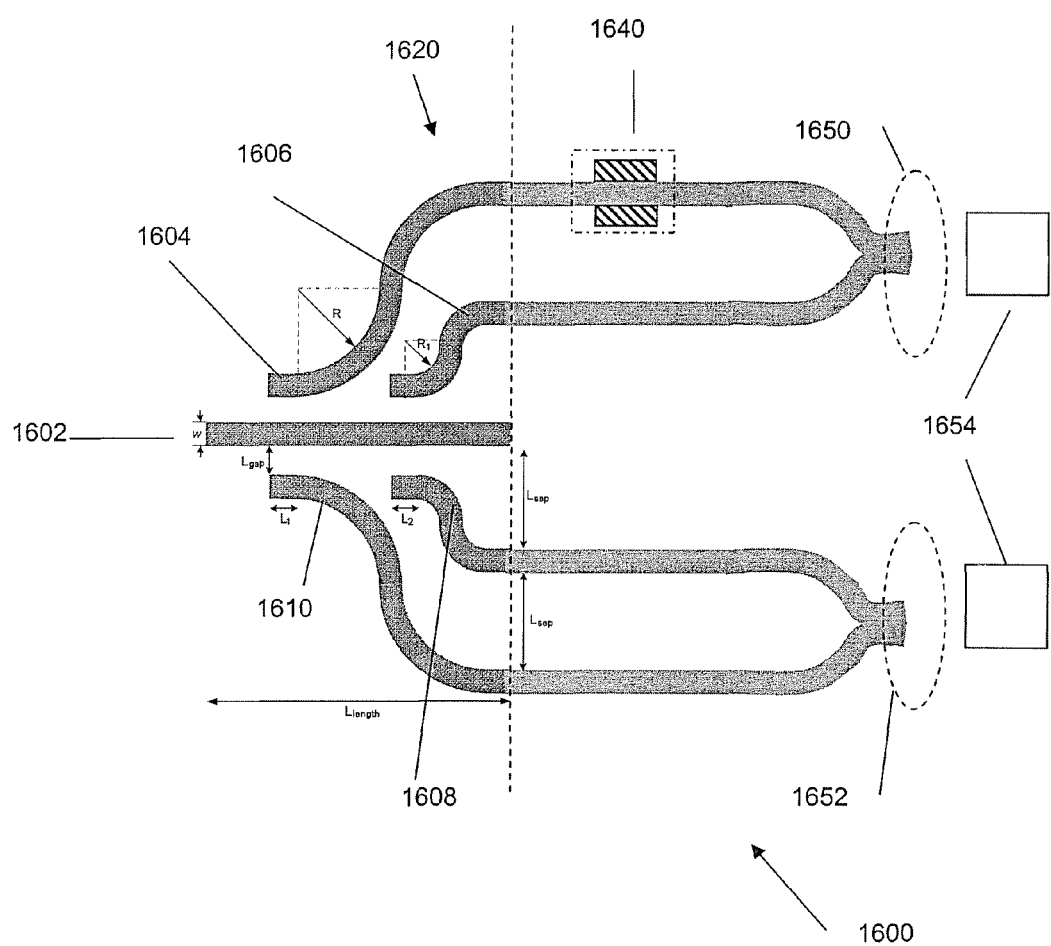
FIG. 16 shows a schematic diagram of an active phase modulator MZI built in accordance with one embodiment of the invention.

In another application, phase modulation can be introduced into a waveguide arm. FIG. 16 shows a schematic diagram of an active phase modulator MZI 1600 built in accordance with one embodiment of the invention.

The active phase modulator MZI 1600 has an optical splitter 1620 having a central waveguide 1602 and four waveguides 1604, 1606, 1608 and 1610. An active photonic bandgap structure 1640 is formed in each of the four waveguides 1604, 1606, 1608 and 1610.

The output portion of the waveguides 1604 and 1606 are joined so that interference between the optical field transmitted in each waveguide 1604 and 1606 occurs at region 1650. It will be appreciated that interference also occurs in the same manner at region 1652 for the waveguides 1608 and 1610.

Photodetectors 1654 can be placed to measure the outputs from the coupling regions 1650 and 1652. While FIG. 16 shows an active phase modulator MZI 1600, it will also be appreciated that a passive configuration can also be designed into another embodiment, where the active structure 1640 is replaced with a passive photonic bandgap structure 140, such as FIG. 1, for sensing applications.

Embodiments of the photonic bandgap devices described herein can be applied in different operations.

The photonic bandgap devices can be deployed in optical communications, which require devices that are low cost, have a high density and provide high data transmission rates. The devices can also be used for biosensing and optical interconnects.

Example embodiments can provide an integrated electronic chip with more waveguide arms in addition to the central waveguide. By closely packing more waveguide arms, multiple tests could be performed simultaneously. The size and sensitivity of the photonic bandgap devices facilitates nanoparticle detection and detection of sensitive analytes.

Other possible applications include diagnostic toolkits to test for GO/NOGO, as well as optical multiplexers and demultiplexers. GO/NOGO applications can be used to determine whether a functional response is met, e.g. serving as an indicator that represent a positive or negative result.

The invention claimed is:

1. An optical splitter comprising:
    a first longitudinal waveguide for receiving an incoming light wave;
    at least first and second pairs of output waveguides, the output waveguides of each pair being disposed on opposite sides of the first waveguide;
    wherein each of the output waveguides of each pair comprises a longitudinal portion disposed parallel to the first waveguide and such that optical power is coupled from the first waveguide into the respective longitudinal portions and the longitudinal portions of output waveguides of the first and second pairs are displaced along a length of the first waveguide;
    wherein each of the output waveguides of each pair further comprises a substantially S-shaped portion continuing from the respective longitudinal portions and such that optical power coupling between the respective S-shaped portions of output waveguides of the first and second pairs is substantially inhibited.

2. The optical splitter as claimed in claim 1, wherein the longitudinal portions of the output waveguides of each pair are disposed at substantially a same distance on the opposite sides of the first waveguide.

3. The optical splitter as claimed in claim 2, wherein the longitudinal portions of the output waveguides of both pairs are disposed at substantially the same distance on the opposite sides of the first waveguide.

4. The optical splitter as claimed in claim 1, wherein a radius of the S-shaped portions of the output waveguides of each pair is chosen such that optical transmission losses are reduced compared to an angled alignment of waveguide portions.

5. The optical splitter as claimed in claim 1, arranged for coupling substantially the same optical power from the light wave into the output waveguides.

6. The optical splitter as claimed in claim 5, wherein substantially all of an input power of the light wave is coupled into the output waveguides.

7. An optical combiner comprising:
    a first longitudinal waveguide;
    at least first and second pairs of input waveguides, the input waveguides of each pair being disposed on opposite sides of the first waveguide;
    wherein each of the input waveguides of each pair comprises a longitudinal portion disposed parallel to the first waveguide and such that optical power is coupled from the respective longitudinal portions into the first waveguide and the longitudinal portions of input waveguides of the first and second pairs are displaced along a length of the first waveguide;
    wherein each of the input waveguides of each pair further comprises a substantially S-shaped portion continuing from the respective longitudinal portions for receiving respective incoming light waves and such that optical power coupling between the respective S-shaped portions of input waveguides of the first and second pairs is substantially inhibited.

8. The optical combiner as claimed in claim 7, wherein the longitudinal portions of the input waveguides of each pair are disposed at substantially a same distance on the opposite sides of the first waveguide.

9. The optical combiner as claimed in claim 8, wherein the longitudinal portions of both pairs of the input waveguides are disposed at substantially the same distance on the opposite sides of the first waveguide.

10. The optical combiner as claimed in claim 7, wherein a radius of the S-shaped portions of the input waveguides of each pair is chosen such that optical transmission losses are reduced compared to an angled alignment of waveguide portions.

11. The optical combiner as claimed in claim 7, wherein substantially all of the respective input powers of the respective light waves is coupled into the first waveguide.

* * * * *